(12) United States Patent
Tsuchiya

(10) Patent No.: US 7,730,242 B2
(45) Date of Patent: Jun. 1, 2010

(54) COMMUNICATION CONVERSION SYSTEM FOR SWITCHING FIRST COMMUNICATION LINES TO SECOND COMMUNICATION LINES BASED ON CHANGE IN VOLTAGE STATE OF DETECTION-USE PIN

(75) Inventor: Shusuke Tsuchiya, Tokyo (JP)

(73) Assignee: Olympus Medical Systems Corp. (JP)

( * ) Notice: Subject to any disclaimer, the term of this patent is extended or adjusted under 35 U.S.C. 154(b) by 133 days.

(21) Appl. No.: 12/042,423

(22) Filed: Mar. 5, 2008

(65) Prior Publication Data

US 2009/0228623 A1 Sep. 10, 2009

(51) Int. Cl.
*G06F 13/12* (2006.01)
*A61B 1/00* (2006.01)

(52) U.S. Cl. ............... 710/72; 710/8; 710/9; 710/10; 710/14; 710/15; 710/16; 710/17; 710/18; 710/19; 710/62; 370/241; 370/467; 455/436; 455/466

(58) Field of Classification Search ............... 710/8–10, 710/14–19, 62, 72; 370/241, 467; 455/436, 455/466
See application file for complete search history.

(56) References Cited

U.S. PATENT DOCUMENTS 6,601,115 B1 7/2003 Yonezawa et al.
6,738,671 B2 * 5/2004 Christophersom et al. .... 607/60
6,922,562 B2 * 7/2005 Ward et al. ................... 455/436
7,318,551 B1 * 1/2008 Mills ........................... 235/441
2002/0055365 A1 * 5/2002 Yamato ....................... 455/466
2008/0019393 A1 * 1/2008 Yamaki ....................... 370/467

FOREIGN PATENT DOCUMENTS

| JP | H05-326086 | 12/1993 |
| JP | H08-234264 | 9/1996 |
| JP | 2005-135654 | 5/2005 |

* cited by examiner

*Primary Examiner*—Tammara Peyton
(74) *Attorney, Agent, or Firm*—Ostrolenk Faber LLP

(57) ABSTRACT

A communication converter includes: a first communication interface making capable of communicating with a medical control device through a predetermined communication cable; a second communication interface making capable of making a connection to a signal distribution unit which is provided in a housing device capable of housing one or more communication converters, and distributes a signal from the medical control device to each of the communication converters; a switch unit for switching communication lines to either a communication line through the first communication interface or a communication line through the second communication interface; a detection unit for detecting whether or not the signal distribution unit is connected to the second communication interface; a switch control unit for controlling the switch unit based on a detection result; and a third communication interface making capable of performing communications with a medical device.

3 Claims, 9 Drawing Sheets

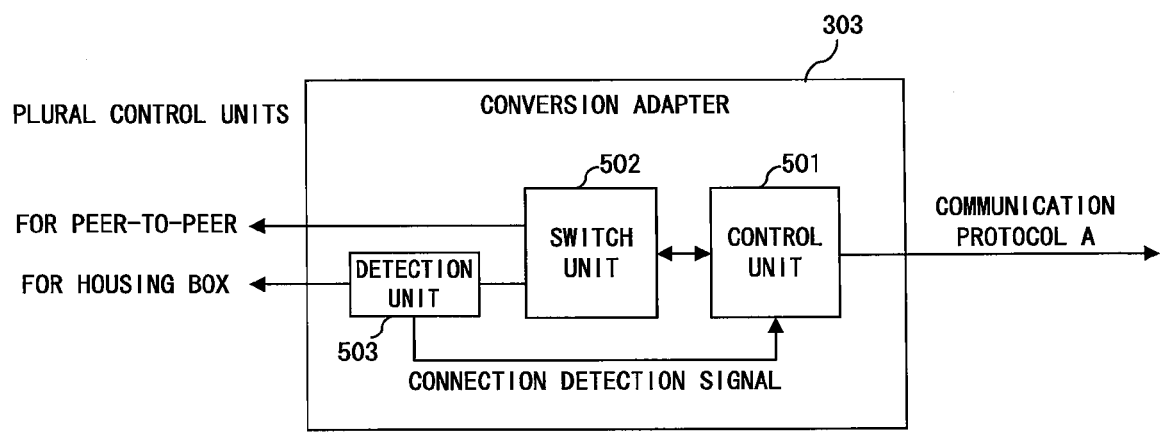
F I G. 6

US 7,730,242 B2

COMMUNICATION CONVERSION SYSTEM FOR SWITCHING FIRST COMMUNICATION LINES TO SECOND COMMUNICATION LINES BASED ON CHANGE IN VOLTAGE STATE OF DETECTION-USE PIN

FIELD OF THE INVENTION

The present invention relates to a communication converter which connects a plurality of medical devices to a medical control device for controlling the medical devices.

BACKGROUND OF THE INVENTION

Recently, surgery is performed using an endoscope operation system having a plurality of medical devices. In an endoscope operation system, when an organization of a living body is removed using an insufflation device for expanding a visceral cavity and a treating device etc. for treating an affected part, and hemostasis is performed using a high frequency cautery device, these treatments can be performed while watching images captured by an endoscope.

The endoscope operation system includes a plurality of medical devices for an endoscope operation, and a system controller for controlling the medical devices, a display operation device, etc. Thus, the endoscope operation system is configured by a plurality of devices, and it is necessary to use a common communication protocol to enable communications between the devices. However, manufacturers of medical devices adopt different communication methods and/or communication protocols for their own medical devices. Therefore, a communication converter is used to convert the communication methods and/or communication protocols to enable communications to be performed between them.

The communication system refers to a system of communications based on the physical or electrical configuration of communications such as infrared communications, USB (Universal Serial Bus) communications, RS-232C communications, Controller Area Network (CAN), or Ethernet communications, etc. A difference in communication system refers to a difference in physical or electrical standards in various communications such as a difference between wireless communication and cable communication, a difference in shape of a connector, etc. (therefore, the difference disables a physical or electrical connection to be performed). A communication protocol refers to a normally adopted communication protocol, that is, a logical connection, as compared with the physical or electrical connection in the above-mentioned communication system.

SUMMARY OF THE INVENTION

The communication converter according to the present invention which converts a communication system and/or a communication protocol to enable communications to be performed between a medical device and a medical control device for controlling the medical device includes:

a first communication interface making capable of communicating with the medical control device through a predetermined communication cable;

a second communication interface making capable of making a connection to a signal distribution unit which is provided in a housing device capable of housing one or more communication converters, and distributes a signal from the medical control device to each of the communication converters;

a switch unit for switching communication lines to either a communication line through the first communication interface or a communication line through the second communication interface;

a detection unit for detecting whether or not the signal distribution unit is connected to the second communication interface;

a switch control unit for controlling the switch unit based on the detection result; and a third communication interface making capable of performing communications with the medical device.

A communication conversion system according to the present invention includes:

a communication converter for converting a communication system and/or a communication protocol to enable communications between a medical device and a medical control device for controlling the medical device; and a housing device capable or housing one or more communication converters.

With the configuration, the communication converter includes:

a first communication interface making capable of communicating with the medical control device through a predetermined communication cable;

a second communication interface for use in communicating with the medical control device when the communication converter is housed in the housing device;

a switch unit for switching communication lines to either a communication line through the first communication interface or a communication line through the second communication interface;

a detection unit for detecting whether or not a predetermined connector of the housing device is connected to the second communication interface;

a switch control unit for controlling the switch unit based on the detection result; and a third communication interface making capable of performing communications with the medical device.

The housing device includes:

a plurality of connectors capable of attaching and removing the second communication interface of the communication converter; and a signal distribution unit for distributing a signal from the medical control device to the communication converter attached to each of the connectors.

BRIEF DESCRIPTION OF THE DRAWINGS

FIG. 6 shows the outline of the internal configuration of the conversion adapter 303 according to an embodiment of the present invention;

DETAILED DESCRIPTION OF THE INVENTION

Figure 1:
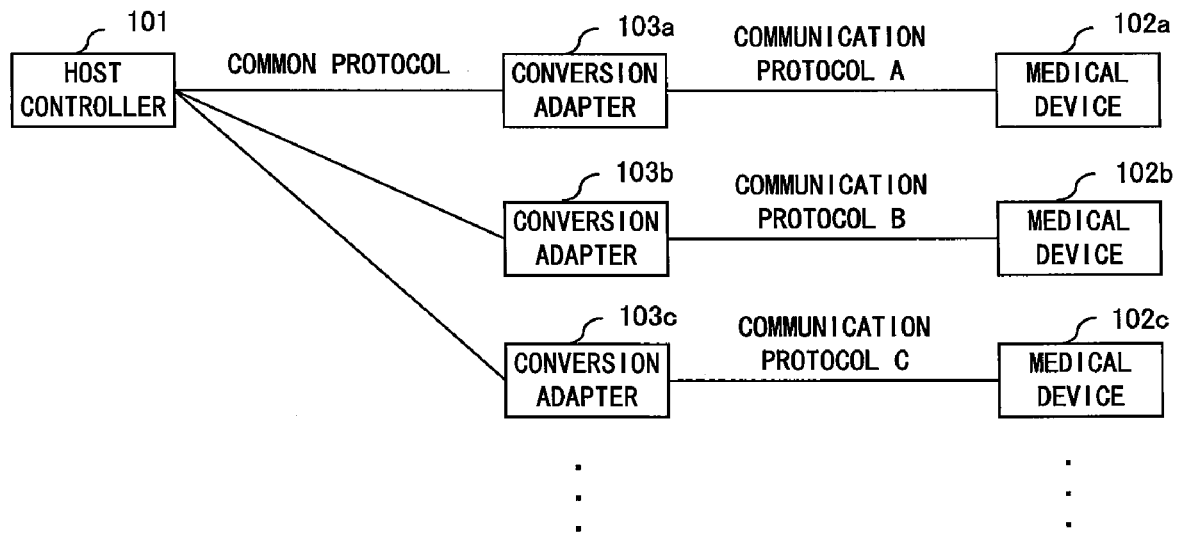
FIG. 1 shows the connection of various medical devices of other manufactures to a host controller of a specific manufacturer.

FIG. 1 shows the connection of various medical devices of other manufactures to a host controller of a specific manufacturer in the conventional technology. Conventionally, when communications among medical devices of different manufactures are integrated, a host controller (system controller) is connected to a medical device through a communication conversion adapter (hereinafter referred to simply as a conversion adapter) because each manufacture uses quite different communication system or communication protocol to each other. FIG. 1 shows an example of connecting a medical device 102a of a manufacturer A, a medical device 102b of a manufacturer B, and a medical device 102c of a manufacturer C to a host controller 101 using conversion adapters 103a, 103b, and 103c corresponding to a communication system and a communication protocol of each manufacturer.

The host controller 101 can use a common communication protocol (hereinafter referred to as a common protocol) for the medical device of the manufacturer of the host controller, and communicate with a medical device having a communication standard corresponding to the common protocol.

On the other hand, the communication interface (I/F) of the medical device 102a of the manufacturer A uses a communication protocol A different from the common protocol and the communication protocols of other manufacturers. Therefore, it is necessary to connect the host controller 101 to the medical device 102a through the conversion adapter 103a for converting communication protocols between the common protocol and the communication protocol A.

In addition, the communication I/F of the medical device 102b of the manufacturer B uses a communication protocol B different from the common protocol and the communication protocols of other manufacturers. Therefore, it is necessary to connect the host controller 101 to the medical device 102b through the conversion adapter 103b for converting communication protocols between the common protocol and the communication protocol B.

The communication I/F of the medical device 102c uses the communication protocol C different from the common protocol and the communication protocols of other manufacturers. Therefore, it is necessary to connect the host controller 101 to the medical device 102c through the conversion adapter 103c for converting communication protocols between the common protocol and the communication protocol C.

Thus, when communications are integrated with the medical devices of other manufactures in the conventional technology, a dedicated conversion adapter is used for each of the medical devices of other manufactures.

Figure 2:
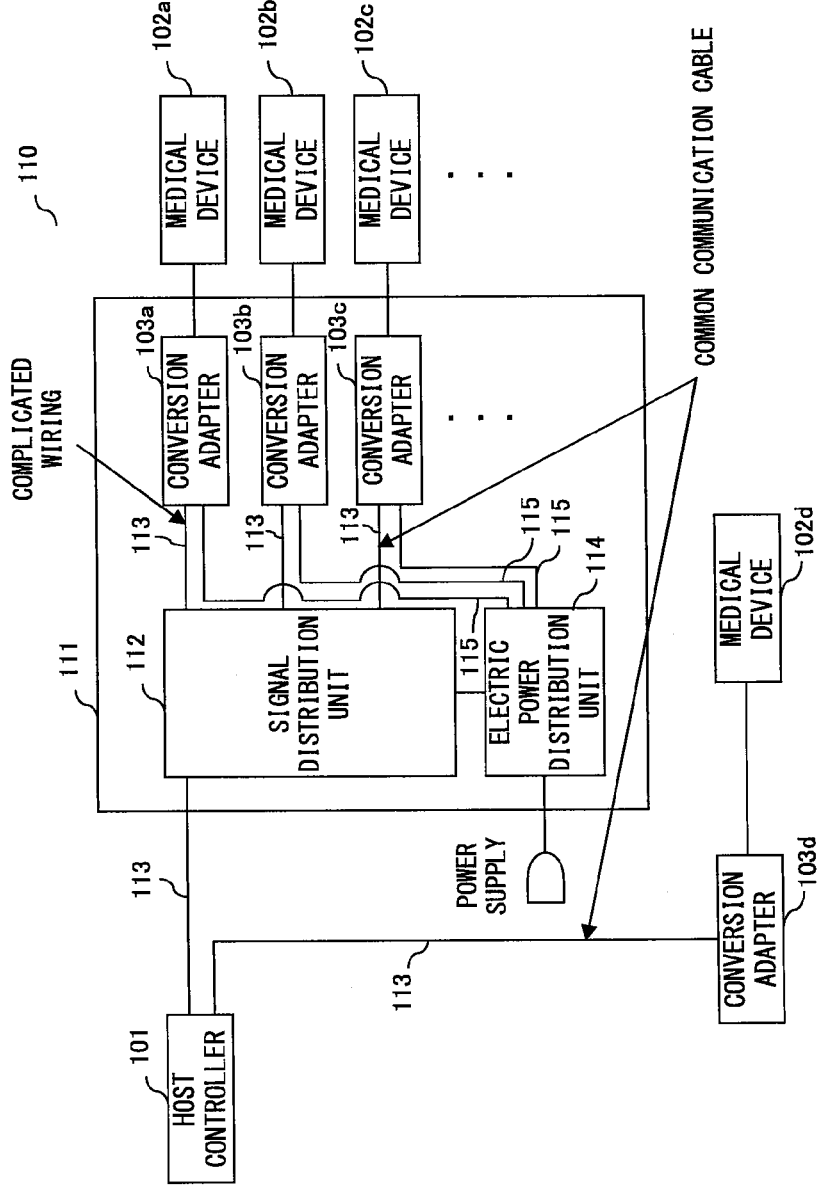
FIG. 2 shows a conventional communication conversion system.

FIG. 2 shows the conventional communication conversion system. A communication conversion system (hereinafter referred to as a conversion system) 110 is configured by a housing box 111 and the conversion adapters 103 (103a, 103b, 103c, . . . ). The host controller 101 and the medical devices 102 (102a, 102b, 102c, . . . ) are connected through the conversion system 110. As described above, the respective communication protocol between the conversion adapters 103 (103a, 103b, 103c, 103d, . . . ) and the medical devices 102 (102a, 102b, 102c, 102d, . . . ) is different from the common protocol or the communication protocols of other manufacturers.

The housing box 111 can house a plurality of conversion adapters 103 (103a, 103b, 103c, . . . ). The housing box 111 includes a signal distribution unit 112, and an electric power distribution unit 114.

The signal distribution unit 112 is a concentrator for centrally connecting communication cables 113. The signal distribution unit 112 is connected to each of the conversion adapters 103 (103a, 103b, 103c, . . . ) through the communication cable 113. The signal distribution unit 112 is connected to the host controller 101 through the communication cable 113. The signal distribution unit 112 can distribute and relays a signal from the host controller 101 to a predetermined medical device. The communication cable 113 is, for example, a cable for a Universal Serial Bus (USB).

The electric power distribution unit 114 supplies electric power to the signal distribution unit 112, or supplies the power to each conversion adapter 103 through the power supply cable 115.

The host controller 101 can be connected directly to the conversion adapter 103d connected to the medical device 102d through the communication cable 113.

Thus, in the conventional technology, the conversion adapter 103 is housed in the housing box 111 to prevent the complicated operations in case the number of uses of the conversion adapter 103 increases. However, since the signal distribution unit 112 in the housing box 111 is conventionally connected to the conversion adapter by a communication system unique to the conversion adapter, it is necessary to make the connection by using the communication cable 113. Additionally, it is necessary to connect the electric power distribution unit 114 to each conversion adapter 103 through the power supply cable 115 to supply electric power to each conversion adapter 103 in the housing box 111. Therefore, in the housing box 111, the wiring between the signal distribution unit 112 and the conversion adapters 103 becomes complicated because of many communication cables 113 and power supply cables 115. As a result, the housing box 111 houses the communication cables 113 and the power supply cables 115, thereby generating a large housing box 111.

Described below is a conversion adapter with the optimum connection system added when a housing box houses a conversion adapter.

Figure 3:
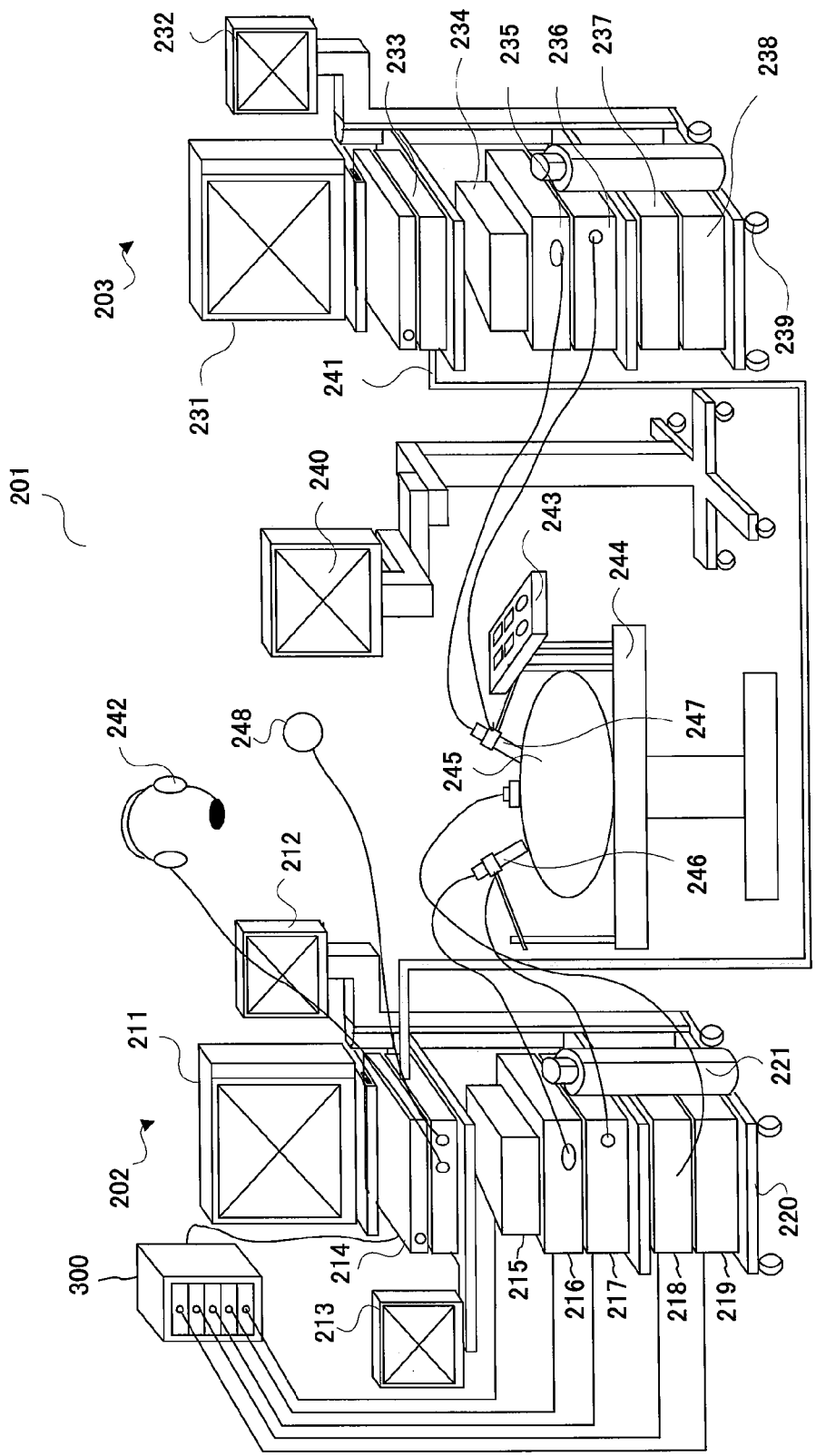
FIG. 3 shows the entire configuration of an endoscope operation system according to an embodiment of the present invention.

FIG. 3 shows the entire configuration of the endoscope operation system according to an embodiment of the present invention. A endoscope operation system 201 is provided on both sides of a bed 244 of a patient 245 with a first endoscope operation system 202, a second endoscope operation system 203, and an operator's wireless remote controller 243.

In the endoscope operation systems 202 and 203, a plurality of endoscope medical devices for performing an observation, inspection, processing, recording, etc. are loaded onto a first trolley 220 and a second trolley 239. A movable stand is loaded with an endoscope display panel 240.

The first trolley 220 includes an endoscope display panel 211, a central display panel 212, a central operation panel device 213, a system controller 214, a recorder 215, a video processor 216, an endoscope light source device 217, an insufflation device 218, and an electrical surgical device 219.

The central operation panel device 213 is arranged in an unsterilized area, and nurses etc. centrally perform operations of medical devices. A mouse, a touch panel, etc. not shown in the attached drawings can be provided for the device. Using the central operation panel device 213, a medical device can be centrally managed, controlled, and operated.

The recorder 215, the video processor 216, the endoscope light source device 217, the insufflation device 218, and the electrical surgical device 219 are connected to the system controller 214 through the conversion system 300 to perform bi-directional communications with the system controller 214.

Additionally, a head set type mike 242 can be connected to the system controller 214. The system controller 214 recognizes the voice input from the head set type mike 242, and can control each device by the voice of an operator. Furthermore, a speaker 248 can be connected to the system controller 214.

The endoscope light source device 217 is connected to a first endoscope 246 through a light guide cable for transmitting illumination light. When the illumination light of the endoscope light source device 217 is supplied to the light guide of the first endoscope 246, it illuminates the affected part etc. in the belly of the patient 245 into which the insertion part of the first endoscope 246 is needled.

The optical image data captured by the camera head of the first endoscope 246 is transmitted to the video processor 216 through the camera cable. The optical image data is signal-processed in the signal processing circuit in the video processor 216, thereby generating a video signal.

The insufflation device 218 provides $CO_2$ gas from a gas tube 221 inside the belly of the patient 245.

The second trolley 239 is loaded with an endoscope display panel 231, a central display panel 232, a expansion unit 233, a recorder 234, a video processor 235, an endoscope light source device 236, and other medical devices 237 and 238 (for example, a ultrasonic processing device, a lithotriosy device, a pump, a shaver, etc.). Each device is connected to the expansion unit 233 via a cable not shown in the attached drawings for bi-directional communications. The system controller 214 is connected to the expansion unit 233 by a expansion cable 241.

The endoscope light source device 236 is connected to a second endoscope 247 through a light guide cable for transmitting illumination light. The illumination light of the endoscope light source device 236 is supplied to the light guide of the second endoscope 247. Then, it illuminates the affected part etc. in the belly of the patient 245 into which the insertion part of the second endoscope 247 is needled.

The optical image data captured by the camera head of the second endoscope 247 is transmitted to the video processor 235 through a camera cable. The optical image data is signal-processed by the signal processing circuit in the video processor 235, thereby generating a video signal. Then the video signal is output to the endoscope display panel 231, and an endoscope image of an affected part etc. is displayed on the endoscope display panel 231.

The system controller 214 can also be controlled by the operator's wireless remote controller 243 with which an operator performs the operation of the device from a sterilized area. In addition, the first trolley 220 and the second trolley 239 can be loaded with other devices (for example, a printer, an ultrasonic observation device, etc.).

Figure 4:
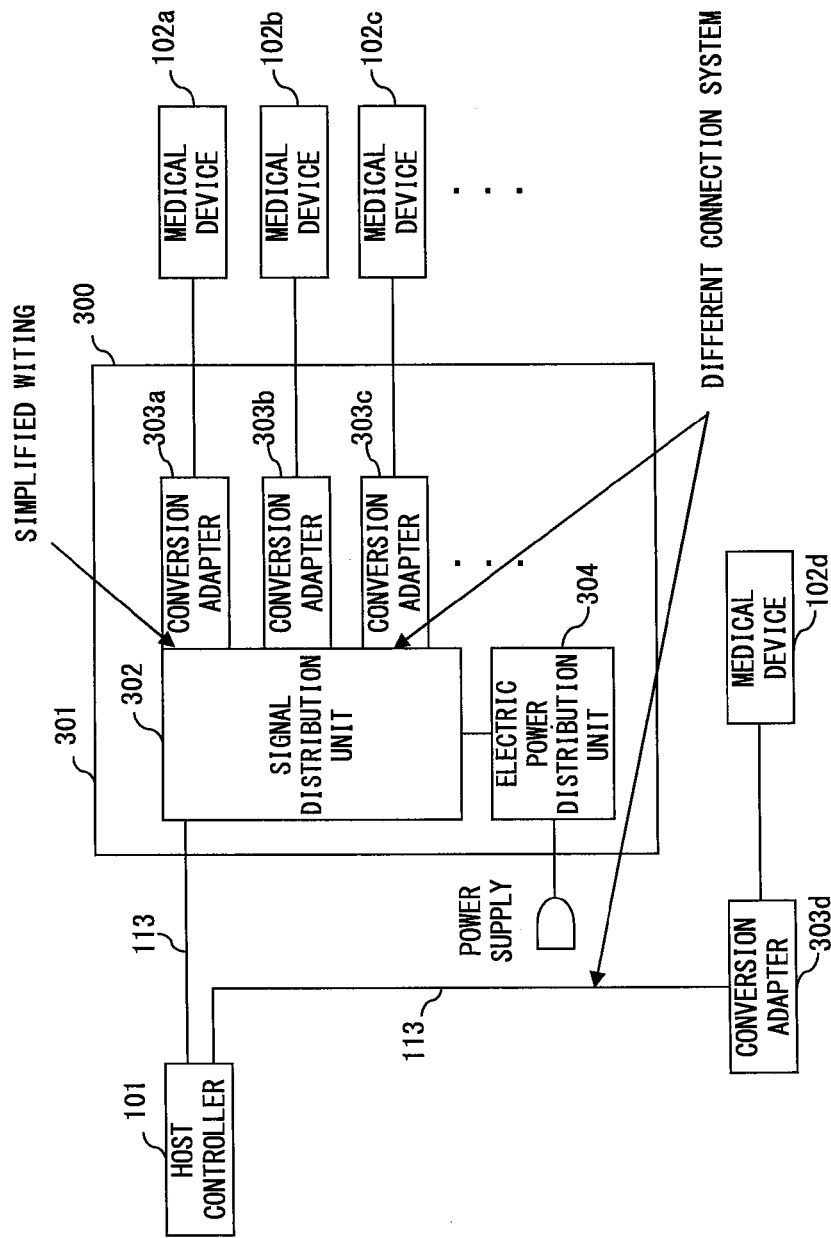
FIG. 4 shows a communication conversion system 300 of an embodiment of the present invention.

FIG. 4 shows the communication conversion system 300 according to an embodiment of the present invention. In the descriptions below, the host controller 101 corresponds to the system controller 214 shown in FIG. 3. The medical devices 102 (102a, 102b, 102c, 102d, ...) correspond to the recorder 215, the video processor 216, the endoscope light source device 217, the insufflation device 218, the electrical surgical device 219, etc. shown in FIG. 3. The host controller 101 is connected to the medical devices 102 (102a, 102b, 102c, ...) through the communication conversion system 300. The connection between the host controller 101 and the communication conversion system 300 and the connection between the host controller 101 and the conversion adapter 303d are made through the respective communication cables 113 for communications using the common protocol.

The communication conversion system 300 is configured by the housing box 111, the conversion adapters 303 (303a, 303b, 303c, ...), the signal distribution unit 302, and the electric power distribution unit 304. As described above, the conversion adapters 303 (303a, 303b, 303c, 303d, ...) and the medical devices 102 (102a, 102b, 102c, 102d, ...) respectively uses communication protocol different from the common protocol and communication protocols of other manufacturers.

A housing box 301 has a housing capable of storing a plurality of conversion adapters 303 (303a, 303b, 303c, ...). The front of the housing box 301 is open so that the conversion adapters can be attached and removed.

The substrate forming the signal distribution unit 302 is provided with a plurality of connectors for directly plugging the conversion adapters 303 (303a, 303b, 303c, ...). By plugging the conversion adapters 303 in the connectors, the signal distribution unit 302 can be bus-connected to the conversion adapters 303. The signal distribution unit 302 is connected to the host controller 101 through the communication cable 113. With the above-mentioned configuration, the signal distribution unit 302 can distributes a signal from the host controller 101 to the medical device 102, and relays a signal from each medical device 102 to the host controller 101.

The electric power distribution unit 304 adjusts the power acquired from the power supply, and supplies the adjusted power to each conversion adapter 303 connected to the signal distribution unit 302. A predetermined pin among the pins of the connectors for connecting the signal distribution unit 302 to the conversion adapters 303 is used for power supply. The electric power distribution unit 304 supplies power to the conversion adapters 303 through the power supply lines and the power supply pins on the signal distribution unit 302.

Thus, by adopting a communicating system for connection by directly plugging the conversion adapters 303 into the signal distribution unit 302 in addition to the connection system using a communication cable normally used for the conversion adapters 303, the wiring between the conversion adapters 303 and the signal distribution unit 302 can be simplified.

Figure 5:
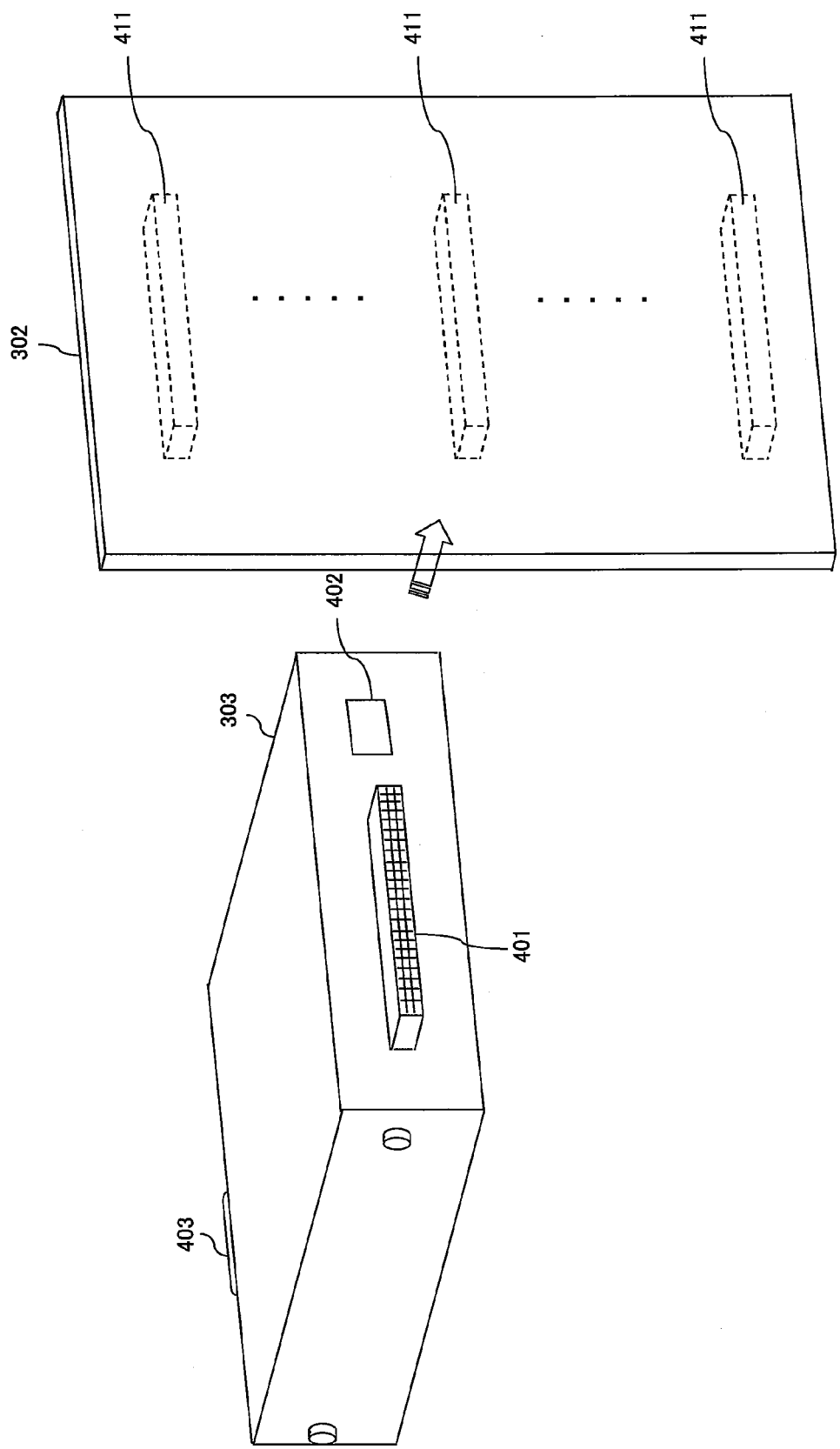
FIG. 5 is a perspective view of the housing of a conversion adapter 303 according to an embodiment of the present invention and shows an example of a connector of a signal distribution unit 302.

FIG. 5 is a perspective view of a housing of the conversion adapter 303 and an example of a connector of the signal distribution unit 302 according to the present embodiment. The conversion adapter 303 is provided with a housing box connector 401, a peer-to-peer connector 402, and a medical device connecting connector 403.

The housing box connector 401 makes a bus-connection to the signal distribution unit 302. For example, it is a DIN connector. The peer-to-peer connector 402 makes a connection to the host controller using the common protocol. For example, it is a USB (type B) connector. The housing box connector 401 can plugs in any connector 411 in a plurality of connectors (for example, DIN connectors) 411 provided for the signal distribution unit 302.

The medical device connecting connector 403 can deal with the communication system and the communication protocol of the medical device to be connected. The medical device connecting connector 403 can be connected to the communication cable 113.

When a connection is made using the peer-to-peer connector 402, a "one-to-one" connection can allow the host controller to communicate with the medical device on a peer-to-peer (one-to-one) basis (refer to the conversion adapter 303d shown in FIG. 4).

On the other hand, when a housing box connector is used for a connection, the host controller can communicate with each medical device by housing a plurality of conversion adapters in the housing box 301. That is, the one-to-n (n is any integer) communication can be established (refer to the conversion adapters 303a, 303b and 303c shown in FIG. 4).

FIG. 6 shows the outline of the internal configuration of the conversion adapter 303 according to an embodiment of the present invention. As shown in FIG. 6, the conversion adapter 303 includes at least a control unit 501, a switch unit 502, and a detection unit 503.

The detection unit 503 detects that the conversion adapter 303 plugs in the connector of the signal distribution unit 302. When the detection unit 503 detects that the adapter plugs in the signal distribution unit 302, it transmits a connection detection signal to the control unit 501.

The control unit 501 includes at least a central processing unit (CPU), memory, etc. The control unit 501 controls the operation of each component configuring the conversion adapter 303, reads and executes a program etc. stored in the memory, and converts communication protocols. The control unit 501 outputs a switch instruction signal to the switch unit 502 according to the connection detection signal from the detection unit 503.

The switch unit 502 switches communication lines to activate one of the communication line through the housing box connector 401 and the communication line through the peer-to-peer connector 402 according to the switch instruction signal from the control unit 501.

Figure 7:
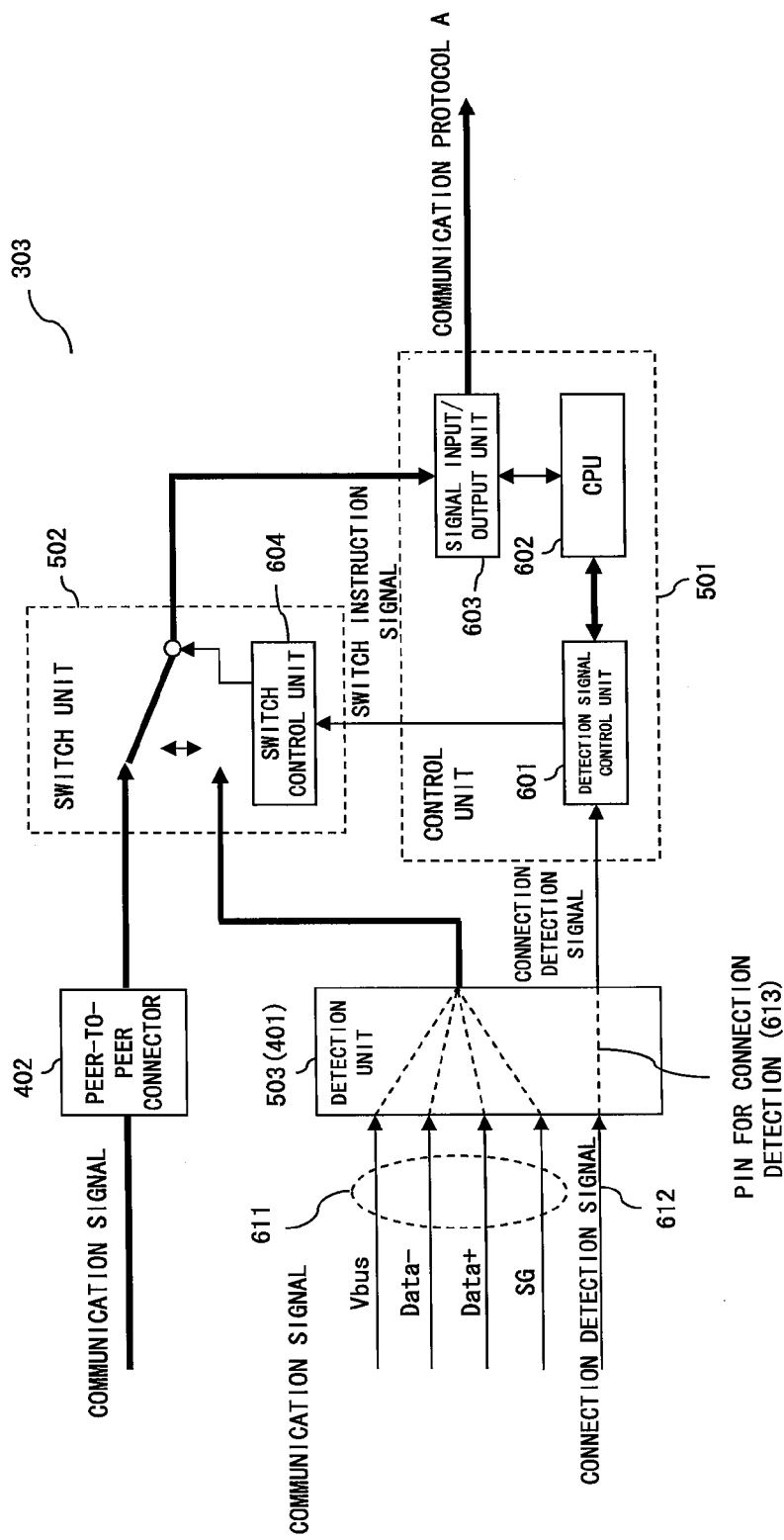
FIG. 7 shows the details of the internal configuration of the conversion adapter 303 according to an embodiment of the present invention.

FIG. 7 shows the details of the internal configuration of the conversion adapter 303 according to an embodiment of the present invention. FIG. 7 shows the internal configuration shown in FIG. 6 in more detail. In the present embodiment, a DIN connector is used as an example of the housing box connector 401. Through the DIN connector, communications can be established by a USB. The detection unit 503 corresponds to the housing box connector 401 (DIN connector), more practically, to a predetermined pin. When the housing box connector 401 is connected to the signal distribution unit 302, the voltage level of the pin changes. The housing box connector 401 has a pin for a communication signal line 611 and a pin 613 for a connection detection signal line 612. The communication signal line 611 is configured by two differential signal lines (D+, D−) and two power supply lines (Vbus, SG). The voltage of the connection detection signal line 612 changes from a high state to a low state when the housing box connector 401 is attached to the signal distribution unit 302. The change of the voltage is output as a connection detection signal to the control unit 501 through the pin 613.

The control unit 501 is configured by a detection signal control unit 601, a CPU 602, and a signal input/output unit 603. The CPU 602 controls the detection signal control unit 601 and the signal input/output unit 603, converts a communication protocol, and performs various other processes. The detection signal control unit 601 outputs a switch instruction signal to the switch unit 502 according to the connection detection signal from the detection unit 503.

The switch unit 502 includes a switch control unit 604. The switch control unit 604 switches between the communication line of the peer-to-peer connector 402 and the communication line of the housing box connector 401 according to the switch instruction signal from the detection signal control unit 601.

Described next is the operation of the conversion adapter 303. When the housing box connector 401 is not attached to the signal distribution unit 302, the switch unit 502 switches to the peer-to-peer connector 402. In this case, the conversion adapter 303 is connected to the communication cable 113 extending from the host controller 101 through the peer-to-peer connector 402. A communication signal based on the common protocol from the host controller 101 is output to the signal input/output unit 603 through the peer-to-peer connector 402 and the switch unit 502. The communication protocol of the control signal is converted by the CPU 602 from the common protocol to a predetermined communication protocol (for example, communication protocol A). The communication signal is output by the signal input/output unit 603 from the medical device connecting connector 403 to a medical device.

Next, when the housing box connector 401 plugs in the connector of the signal distribution unit 302, the voltage of the connection detection signal line 612 changes from high level to low level, or from low level to high level. The change of the voltage is output as a connection detection signal to the detection signal control unit 601 through the pin 613. The detection signal control unit 601 outputs a switch instruction signal to the switch control unit 604 according to the connection detection signal. The switch control unit 604 switches the communication line from the peer-to-peer connector 402 to the housing box connector 401 according to the switch instruction signal from the detection signal control unit 601. In this case, the communication signal based on the common protocol from the host controller 101 is transmitted to the signal distribution unit 302 of the housing box 301. The signal distribution unit 302 routes the communication signal, and outputs the signal to the conversion adapter 303 to which the destination medical device is connected. The communication signal is output to the signal input/output unit 603 through the housing box connector 401 and the switch unit 502. The CPU 602 converts the communication protocol of the communication signal from the common protocol to a predetermined communication protocol (for example, a communication protocol A). The signal input/output unit 603 outputs the communication signal from the medical device connecting connector 403 to the medical device.

When the housing box connector 401 is removed from the signal distribution unit 302, the voltage of the connection detection signal line 612 changes from low level to high level, and the change of the voltage is output as a connection detection signal to the detection signal control unit 601 through the pin 613. The detection signal control unit 601 outputs a switch instruction signal to the switch control unit 604 according to the connection detection signal. The switch control unit 604 switches the communication line from the housing box connector 401 to the peer-to-peer connector 402 according to the switch instruction signal from the detection signal control unit 601.

According to the configurations shown in FIGS. 6 and 7, since the control unit 501 performs switch control, the control is performed independent of the specifications of the switch unit 502. That is, by providing the detection signal control unit 601, the detection signal control unit 601 can output a signal based on the specifications of the switch control unit 604 when the connection detection signal is received. That is, the CPU 602 can control the switch unit 502 with programmability.

Thus, by adding to the conversion adapter the optimum connecting method when the conversion adapter is stored in the housing box, the connections of the power supply cables and the communication cables can be simplified. In addition, since the present invention can also be applied to the conventional connection system, the optimum layout can be structured for each hospital.

Described next is an example of a variation of an embodiment of the present invention. In the following descriptions, only the portions different from the above-mentioned embodiments are described, and the same descriptive portions are omitted.

Figure 8:
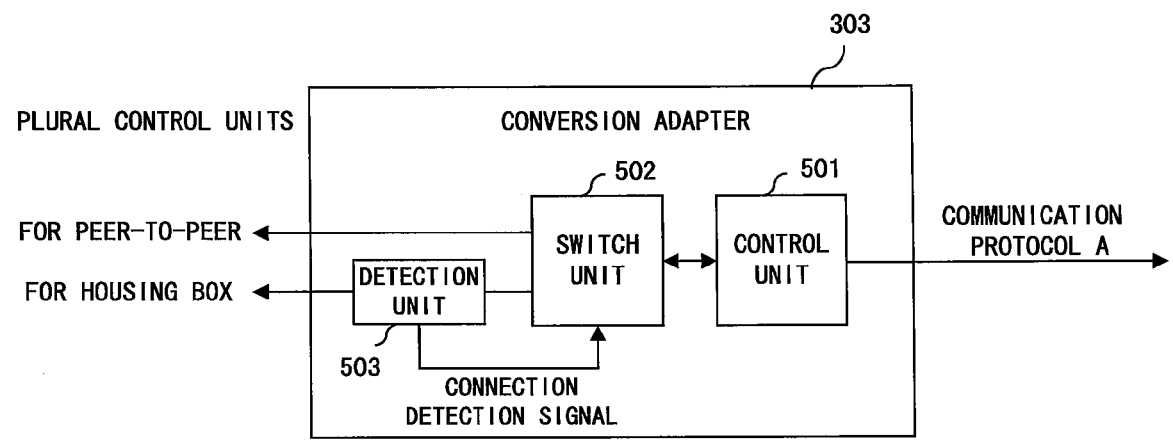
FIG. 8 shows the outline of the internal configuration of the conversion adapter 303 according to an embodiment (variation) of the present invention.

FIG. 8 shows the outline of the internal configuration of the conversion adapter 303 according to an embodiment (variation example) of the present invention.

The difference between FIGS. 6 and 8 is that the connection detection signal is output from the detection unit 503 to the switch unit 502.

Figure 9:
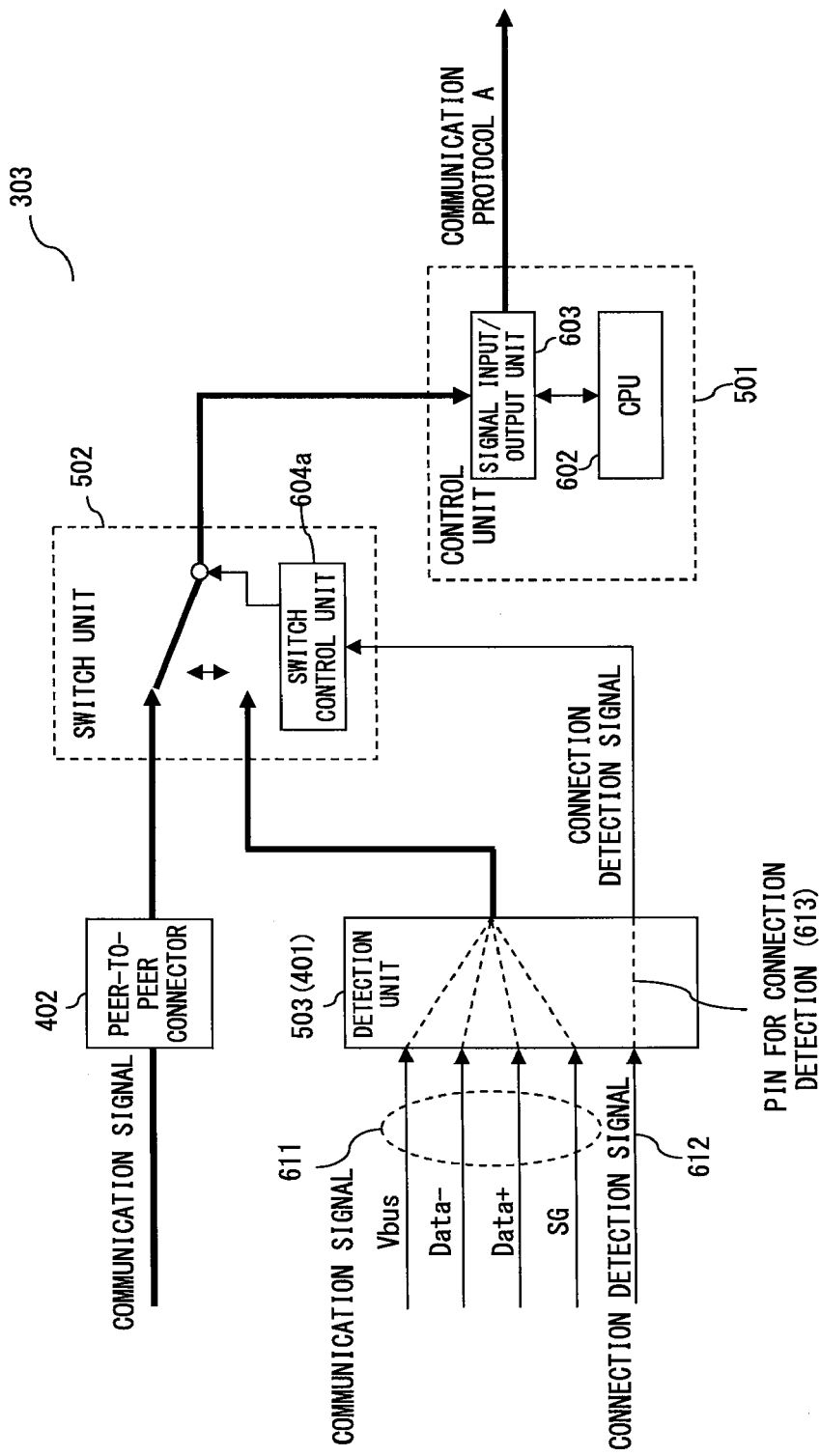
FIG. 9 shows the details of the internal configuration of the conversion adapter 303 according to an embodiment (variation) of the present invention.

FIG. 9 shows details of the internal configuration of the conversion adapter 303 according to an embodiment (variation example) of the present invention. FIG. 9 shows the internal configuration shown in FIG. 8 in more detail. The differences between FIGS. 7 and 9 are that the control unit 501 includes no detection signal control unit 601, and a connection detection signal is output from the detection unit 503 to a switch control unit 604a.

The switch control unit 604a switches between the communication line of the peer-to-peer connector 402 and the communication line of the housing box connector 401 according to the connection detection signal from the detection unit 503. Other operations are the same as those shown in FIG. 7.

According to the embodiment, as compared with FIGS. 6 and 7, the configuration of the control unit 501 can be simpler. However, it depends on the specifications of the switch unit 502.

According to the present embodiment, the communication conversion system includes a communication converter and a housing device. The communication converter can convert a communication system and/or a communication protocol to enable communications between a medical device and a medical control device for controlling the medical device. The housing device can house one or more communication converters.

The communication converter, in the present embodiment for example, corresponds to the conversion adapter 303. The communication converter includes a first communication interface, a second communication interface, a switch unit, a detection unit, a switch control unit, and a third communication interface.

The first communication interface enables communications with the medical control device through a predetermined communication cable. The first communication interface corresponds to the peer-to-peer connector 402 according to the present embodiment for example.

The second communication interface is used for communications with the medical control device when the communication converter is stored in the housing device. The second communication interface corresponds to the housing box connector 401 according to the present embodiment for example.

The switch unit switches communication lines to either the communication line through the first communication interface or the communication line through the second communication interface. The switch unit corresponds to the switch unit 502 according to the present embodiment for example.

The detection unit detects whether or not the signal distribution unit is connected to the second communication interface. The detection unit corresponds to the detection unit 503 according to the present embodiment for example.

The switch control unit controls the switch unit based on the detection result. The switch control unit corresponds to the detection signal control unit 601 or the switch control unit 604a according to the present embodiment.

The third communication interface enables communications with the medical device. The third communication interface corresponds to the medical device connecting connector 403 according to the present embodiment for example.

The housing device corresponds to the housing box 111 according to the present embodiment for example. The housing device includes a plurality of connectors and a signal distribution unit.

The connector can be attached and removed to and from the second communication interface of the communication converter. The second communication interface is connected to the connector using a connection system in which a connector format (for example, a bus connection system) is different from that of the first communication interface. The connector corresponds to the connector 411 according to the present embodiment for example.

The signal distribution unit distributes a signal from the medical control device to a communication converter attached to each connector. The signal distribution unit corresponds to the signal distribution unit 302 according to the present embodiment for example.

According to the present embodiment, the conversion adapter is provided with a communication interface capable of dealing with a connection system for peer-to-peer (one-to-one) and also a connection system for a housing box (one-to-n) (n is an arbitrary integer). Thus, by adding to the conversion adapter the optimum connection system when it is housed in the housing box, the connections of the power supply cables and the communication cables can be simplified, thereby downsizing the housing box. Depending on the connection environment of the host controller and the medical device in each hospital and the mounting space of a housing box, a connection system to be used can be selected. Thus, the optimum layout can be structured for each hospital.

What is claimed is:

1. A communication converter which converts a communication system and/or a communication protocol to enable communications between a medical device and a medical control device for controlling the medical device, comprising:
   a first communication interface configured and operable for communicating with the medical control device through a predetermined communication cable;
   a second communication interface configured and operable for making a connection to a signal distribution unit which is provided in a housing device capable of housing one or more communication converters, and distributes a signal from the medical control device to each of the communication converters;
   a switch unit for switching communication lines to either a first communication line through the first communication interface or a second communication line through the second communication interface;
   a detection unit for detecting whether or not the signal distribution unit is connected to the second communication interface;
   a switch control unit for controlling the switch unit based on a detection result; and
   a third communication interface configured and operable for performing communications with the medical device, wherein
   the second communication interface is a connector which enables a connection to be made to the signal distribution unit by a connection system using a connector having a format different from that of the first communication interface, the detection unit is a detection-use pin included in the connector formed by a plurality of pins, and the detection unit detects a change in a voltage state of the detection-use pin caused when the connector is connected to the signal distribution unit in order to detect whether or not the signal distribution unit is connected to the second interface, and the switch control unit controls the switch unit to switch the communication lines from the first communication line to the second communication line when it is determined based upon the detection result of the detection unit that the signal distribution unit is connected to the second communication interface.

2. A communication conversion system, comprising:

a communication converter for converting a communication system and/or a communication protocol to enable communications between a medical device and a medical control device for controlling the medical device; and a housing device capable of housing one or more communication converters, wherein the communication converter comprises:

a first communication interface configured and operable for communicating with the medical control device through a predetermined communication cable;

a second communication interface for use in communicating with the medical control device when the communication converter is housed in the housing device;

a switch unit switching communication lines to either a communication line through the first communication interface or a communication line through the second communication interface a detection unit detecting whether or not a predetermined connector of the housing device is connected to the second communication interface;

a switch control unit controlling the switch unit based on a detection result; and a third communication interface configured and operable for performing communications with the medical device; and the housing device comprises:

a plurality of connectors capable of attaching and removing the second communication interface of the communication converter; and a signal distribution unit distributing a signal from the medical control device to the communication converter attached to each of the connectors.

3. The system according to claim 2, wherein the second communication interface is connected to the connector by a connection system using a connector having a different format from that of the second communication interface.

* * * * *